(12) United States Patent
Jensen et al.

(10) Patent No.: US 6,635,050 B1
(45) Date of Patent: Oct. 21, 2003

(54) OSTOMY SITING DEVICE

(75) Inventors: Henrik Jessen Jensen, Birkeroed (DK); Eskil Hoejland Olsen, Humelbaek (DK); Hans Olsen, Hoersholm (DK)

(73) Assignee: Coloplast, A/S, Humlebaek (DK)

( * ) Notice: Subject to any disclaimer, the term of this patent is extended or adjusted under 35 U.S.C. 154(b) by 0 days.

(21) Appl. No.: 09/926,455

(22) PCT Filed: May 3, 2000

(86) PCT No.: PCT/DK00/00223

§ 371 (c)(1),
(2), (4) Date: Nov. 6, 2001

(87) PCT Pub. No.: WO00/67683

PCT Pub. Date: Nov. 16, 2000

(30) Foreign Application Priority Data

May 6, 1999 (DK) .......................................... 1999 00619

(51) Int. Cl.[7] .............................. A61B 17/00; A61F 5/44
(52) U.S. Cl. ........................... 606/1; 604/332; 604/344; 606/116
(58) Field of Search ............................ 606/1, 116, 117, 606/186; 604/332, 338, 344

(56) References Cited

U.S. PATENT DOCUMENTS

| | | | |
|---|---|---|---|
| 3,983,298 A | | 9/1976 | Hahn et al. .................. 428/355 |
| 4,505,976 A | | 3/1985 | Doehnert et al. ............. 428/355 |
| 4,680,210 A | * | 7/1987 | Corcoran ................... 428/42.3 |
| 4,860,331 A | * | 8/1989 | Williams et al. ............. 606/130 |
| 4,892,096 A | * | 1/1990 | Narayanan et al. ............. 606/1 |
| 5,203,806 A | * | 4/1993 | Broida ........................ 604/338 |
| 5,306,271 A | * | 4/1994 | Zinreich et al. ................ 606/1 |
| 5,312,382 A | | 5/1994 | Metz ........................... 604/338 |
| 5,618,276 A | * | 4/1997 | Leise et al. .................. 604/336 |
| 5,693,035 A | * | 12/1997 | Leise et al. .................. 604/333 |
| 5,722,965 A | * | 3/1998 | Kuczynski ................... 604/338 |
| 5,833,649 A | * | 11/1998 | Atef ............................. 604/500 |
| 5,928,797 A | * | 7/1999 | Vineberg ..................... 401/132 |
| 6,056,737 A | * | 5/2000 | Rosen ............................ 606/1 |
| 6,074,721 A | * | 6/2000 | Moore et al. ............... 428/42.1 |
| 6,113,561 A | * | 9/2000 | Augustine ..................... 607/96 |
| 6,143,945 A | * | 11/2000 | Augustine et al. ............ 607/96 |
| 6,274,787 B1 | * | 8/2001 | Downing ..................... 602/41 |
| 2003/0040706 A1 | * | 2/2003 | Kuracina et al. ............. 604/116 |

FOREIGN PATENT DOCUMENTS

EP     0 800 804     10/1997

\* cited by examiner

*Primary Examiner*—Linda C. M. Dvorak
*Assistant Examiner*—Jocelyn Ram
(74) *Attorney, Agent, or Firm*—Jacobson Holman PLLC

(57) ABSTRACT

An ostomy siting device for determining and marking the position of a possible stoma comprising a stoma simulating first element and a second element simulating an adhesive wafer of an ostomy appliance and an optionally separately detachable collecting bag, said ostomy siting device having on the proximal side an adhesive surface for removable adhering to the abdominal skin of an ostomate to be provided a readily repositionable and reusable system for simulating the placement and physical configuration of the stoma and the collection system and for marking the optimum position of the stoma to be.

28 Claims, 4 Drawing Sheets

OSTOMY SITING DEVICE

This is a nationalization of PCT/DK00/00223, filed May 3, 2000 and published in English.

BACKGROUND OF THE INVENTION

1. Field of the Invention

The present invention relates to a device for locating and marking the optimal position of an artificial intestinal or urethral opening, e.g. a stoma before the operation is carried out.

In connection with surgery for a number of diseases in the gastrointestinal tract a consequence is, in many cases, that the colon, the ileum or the urethra has been exposed surgically and the patient is left with an abdominal stoma. Such artificial intestinal openings or fistulae cannot be controlled at will and are therefore of necessity incontinent and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Such appliances may be two-piece or one-piece appliances. In both types of appliances, a body side member is attached to the wearer's abdomen, and optionally a receiving member or bag is attached to the body side ostomy member for receiving exudates from the ostomy in case of a two-piece appliance.

The quality of life for the patient after this kind of surgery is very much dependent on the placing of the stoma, which can be varied within limits determined by physiological criteria to take into account the patient's natural folds in the abdominal skin, etc.

2. Description of the Related Art

Determination of the site for placing the stoma is normally carried out prior to the operation by a nurse having experience in this field by observing the patient in different postures, e.g. sitting, standing and bending over, finding the less critical area and marking the position for placing the stoma on the patient's skin e.g. with a permanent marking ink.

This method, however, does only to a limited degree take into account the patient's preferred clothing style, position of optional belts, etc. Furthermore, the patient has very little chance of evaluating the consequence of the placing of the stoma, the more so, as the patient is only attentive to this situation on a theoretical level at this stage.

It is therefore desirable to provide a device which more clearly can illustrate to the nurse and the patient the consequences of different sitings of an ostomy and to enable the choice of siting which will give the least possible degree of discomfort.

It is an object of the invention to provide a device which can simulate the stoma in a chosen position, also representing the adhesive wafer and the collecting device, in a way that allows the normally dressed patient and the nurse to thoroughly test different positions of the stoma and evaluate the pros and cons of each position, thereby ensuring the optimal siting and hence, quality of life for the patient after surgery.

It would seem obvious to carry out this simulation with the adhesive wafers and collecting units intended for use by ostomates.

These products, however, are not suitable for repositioning, as the adhesives normally used for this purpose are designed to adhere strongly to the patient's skin over an extended period of time, thereby giving an undesirable pain when removed to be repositioned, which will inherently be a limiting factor to the number of trials accepted by the patient. Also, the adhesive forces of such products will deteriorate rapidly after the first removal for repositioning, thereby increasing the number of wafers necessary and hence, the cost of a thorough investigation.

It has now been found that the above drawbacks of known principles of preparation for operation may be overcome by providing a readily repositionable and reusable system for simulating the placement and physical configuration of the stoma and the collection system and for marking the optimum position of the stoma to be.

SUMMARY OF THE INVENTION

The present invention relates to an ostomy siting device for determining and marking the position of a possible stoma.

The ostomy siting device comprises a stoma simulating first element and a second element simulating an adhesive wafer of an ostomy appliance and an optional separately detachable collecting bag, having on the proximal surface an adhesive suitable for repeated adhering to and removal from the abdominal skin of an ostomate to be.

The invention furthermore relates to an ostomy siting device having a centrally placed hole or cavity, which may be communicating only with the proximal side of the adhesive disc. The cavity may contain a marking ink and may be provided with a valve to prevent unintentional marking of the skin, the ink may be confined in a separately mountable container, the proximal side of the cavity may be provided with a felt-like printing pad or the cavity may contain a transferable marking label.

Still further, the invention relates to an ostomy pi siting device having a centrally placed through-bore having a diameter suitable for centering and guiding a marking pen.

BRIEF DESCRIPTION OF THE DRAWINGS

The invention is explained in more detail with reference to the drawings in which.

DETAILED DESCRIPTION OF THE PRESENT INVENTION

Figure 1:
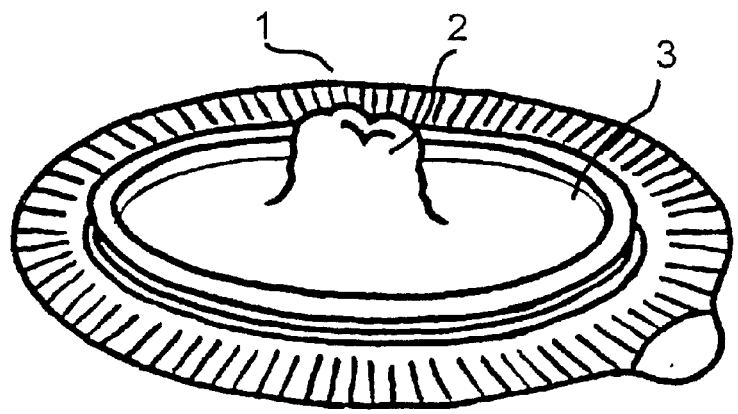
FIG. 1 shows a perspective view of an ostomy siting device for determining and marking the position of a possible stoma.

The present invention relates in a first aspect to an ostomy siting device for determining and marking the position of a possible stoma comprising a stoma simulating first element and a second element simulating an adhesive wafer of an ostomy appliance and an optionally separately detachable collecting bag, said ostomy siting device having on the proximal side an adhesive surface for adhering to the abdominal skin of an ostomate to be. When comprising a separately detachable collecting bag, the ostomy siting device is provided with a suitable coupling system for the bag known per se.

In a preferred embodiment, the ostomy siting device comprises separate first and second elements so that said first element can be placed in direct contact with the user's skin through a centrally placed hole in said second element, so that the elements are separately removable.

In a more preferred embodiment, said adhesive is suitable for repeated adhering to and removal from the patient's skin.

In an even more preferred embodiment, the adhesive is, in order to overcome the unpleasantness normally connected with repeated repositioning of the device to determine the best position for the stoma to be, made from a pressure sensitive adhesive based on silicone rubber, e.g. of the type described in U.S. Pat. No. 3,983,298, which has high tack, good adhesive strength, and an exceptional resistance to creep, even at elevated temperatures.

To overcome difficulties in obtaining a proper bond between the adhesive and the wafer, the entire marking device may be made from silicone rubber, which can be balanced in hardness and elasticity to simulate the adhesive wafers normally intended for ostomy use. In this embodiment, the distal surface of the ostomy siting device may be covered with a non-tacky polymer film to prevent the device from sticking to e.g. clothes.

One embodiment allows the marking of the position through a centrally placed hole having a diameter suitable for a marking pen, when a satisfactory position for the stoma to be has been found.

Another embodiment includes a marking device having a cavity communicating only with the proximal side of the adhesive wafer. In a further embodiment, the cavity may carry a transferable marking label. Still further, in a preferred embodiment, the cavity is containing a marking ink. In this embodiment, the position is marked by squeezing the central part of the ostomy siting device, whereby a small amount of the marking ink is pressed out onto the patient's skin. The cavity may, in a more preferred embodiment, be provided with a valve, preferably so designed, that it may be activated only by pressing opposed sides of the first element In a preferred embodiment the marking ink is suitable for a permanent marking of the skin and is waterproof and resistant to desinfectants.

To avoid unwanted marking, the central part of the first element may be retracted a certain distance from the proximal surface of the device, and the silicone material surrounding the cavity may be made with a sufficient stiffness to allow the central part of the cavity to come into contact with the skin only when the outside pressure is higher than 3 Newtons.

To ease handling of the device the ink may be confined to a felt-like printing pad.

In another embodiment, the cavity may be provided with a valve which, in a preferred embodiment, is operable only when simultaneously pressing opposing sides of said first element.

Still further, the cavity may be provided with a separately mountable ink container which may be provided with a seal.

To control the breaking of the seal, said seal may be provided with cross- or star-shaped impressions serving as breaking initiators, and to prevent uncontrolled release of ink, the proximal side of said seal may be provided with a felt-like printing pad.

For breaking the seal, the distal part of the ink container may be provided with an internally mounted sharp point for breaking the seal, said distal part being collapsible when mounted in the device by a force not greater than the force needed for bringing the central part of the cavity into contact with the skin.

In the embodiments comprising a felt-like printing pad, the pad may be covered with a protecting cover strip having a lobe extending outside the device, so that when marking is desired the strip can be removed without moving the siting device from the desired position.

DESCRIPTION OF THE DRAWINGS AND THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scone of the invention will become apparent to those skilled in the art from this detailed description.

FIG. 1 shows a perspective view of an ostomy siting device (1) for determining and marking the position of a possible stoma with a first stoma simulating element (2) and a second element (3) simulating an adhesive wafer of an ostomy appliance.

Figure 2:
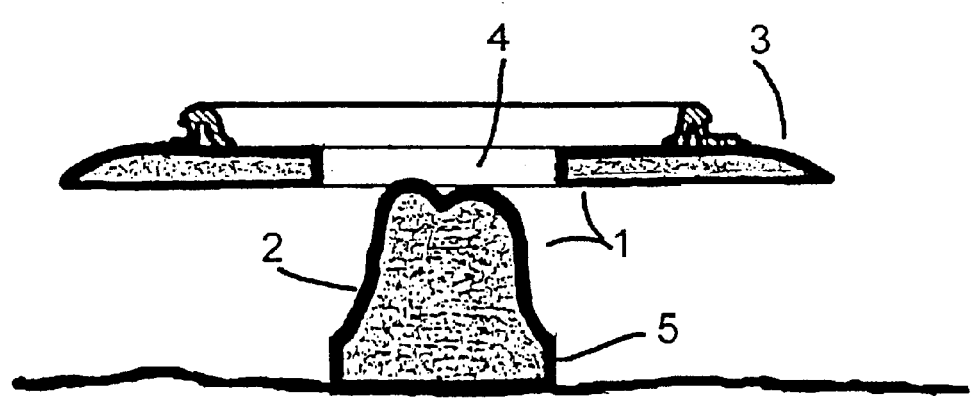
FIG. 2 shows a diametrical sectional view of an ostomy siting device for determining and marking the position of a possible stoma in which a first element can be placed in direct contact with the user's skin through a centrally placed hole in a second element, so that the elements are separately removable.

FIG. 2 shows a diametrical sectional view of an ostomy siting device for determining and marking the position of a possible stoma in which the second element (3) has a centrally placed hole (4) having a greater diameter than the part (5) of the first element (2) adapted to contact the skin through which said first element (2) can be placed in direct contact with the user's skin, so that the elements (2) and (3) are separately removable.

Figure 3:
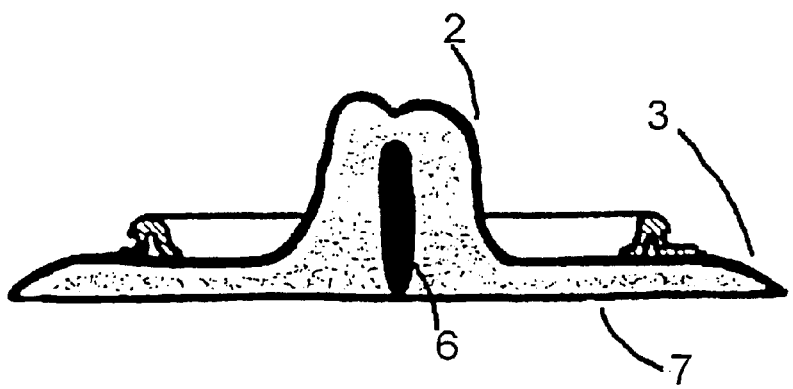
FIG. 3 shows the device in which the first element is provided with a cavity communicating only with the proximal side of the adhesive disc, said cavity containing a marking ink.

FIG. 3 shows the device in which the first element (2) is provided with a centrally placed cavity (6) communicating only with the proximal side (7) of the ostomy siting device, said cavity containing a marking ink.

Figure 4:
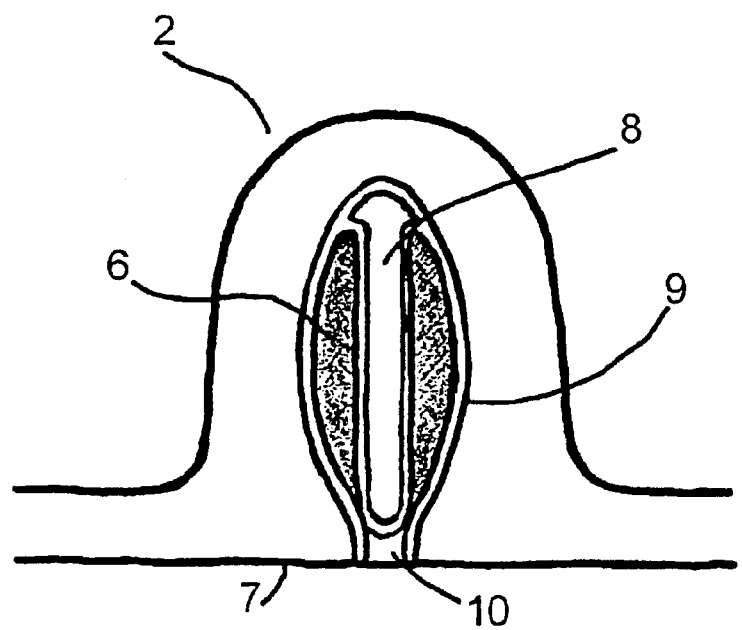
FIG. 4 shows the first element of the device provided with a valve stem and a cage-like reinforcement of the cavity walls.

FIG. 4 shows the first element (2) of the device in which said cavity (6) is provided with a valve stem (8) sealing an opening (10) in the proximal side (7) of the device and a cage-like reinforcement (9) of the cavity walls. The valve stem (8) and the ribs of the cage-like reinforcement (9) are made from any suitable plastics material having a modulus of elasticity significantly higher than the surrounding silicone material of the first element (2). This design will allow the first element (2) to bend without lifting the valve stem (8) when influenced by unilateral forces, so that the valve is operable only when simultaneously pressing opposing sides of said first element.

Figure 5:
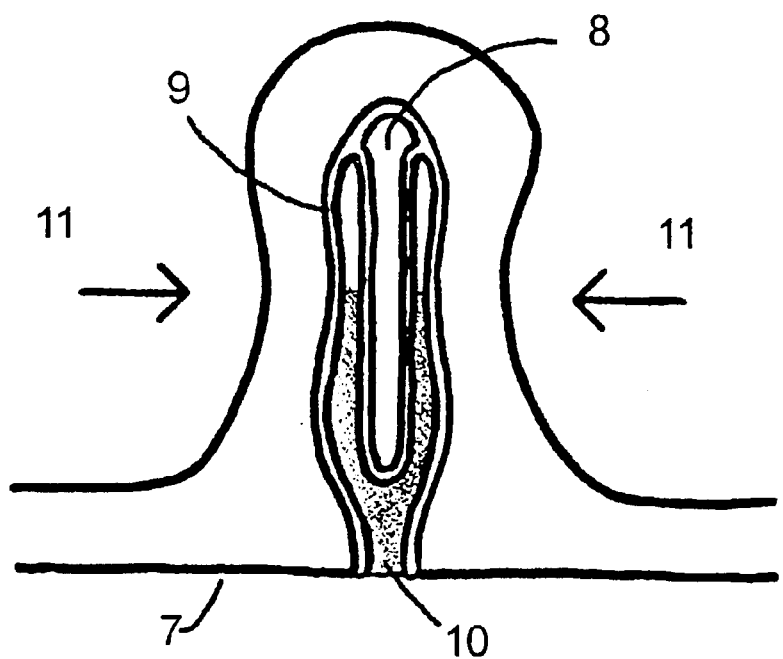
FIG. 5 shows the device of FIG. 4 when activated by simultaneously pressing opposed sides of the first element, FIG. 6. shows the first element of the device in which the marking ink is confined to a felt-like printing pad.

FIG. 5 shows the device of FIG. 4 when activated by forces (11) simultaneously pressing opposed sides of the first element, straightening the ribs (9) and thereby lifting the valve stem (8) from the opening (10) in the proximal side (7) of the device.

Figure 6:
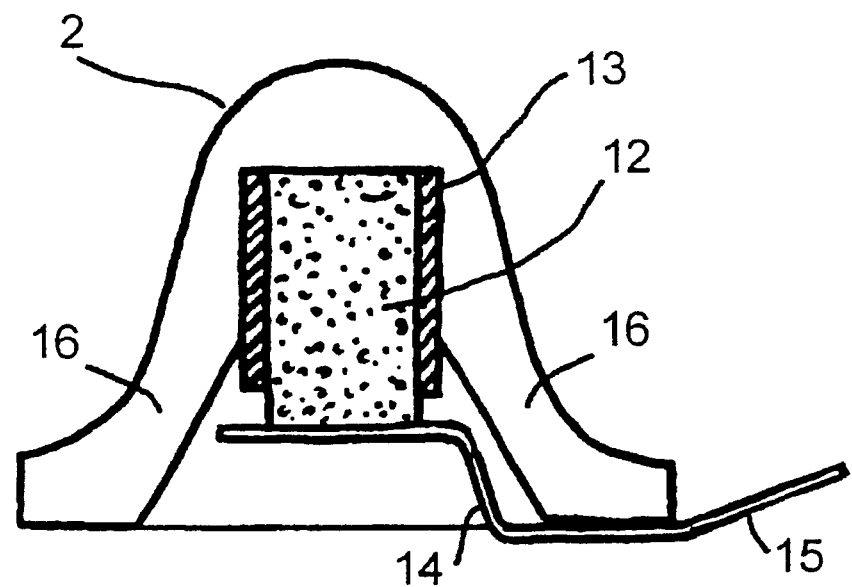

FIG. 6. shows the first element (2) of the device in which the marking ink is confined to a felt-like printing pad (12) in an insert (13). In order to prevent unintended marking, the proximal surface of the felt-like printing pad (12) may be covered with a protecting cover strip (14) having a lobe or ear (15) extending outside the device or outside the first element (2), whichever is applicable, so that when marking is desired the strip can be removed without moving the siting device from the desired position on the skin. In order to further prevent unintentional marking, the silicone material (16) surrounding the proximal zone of the cavity has sufficient stiffness to allow the central part of the cavity and the printing pad (12) to come into contact with the skin only when the force pressing on top of the first element (2) is higher than e.g. 3 Newtons.

Figure 7:
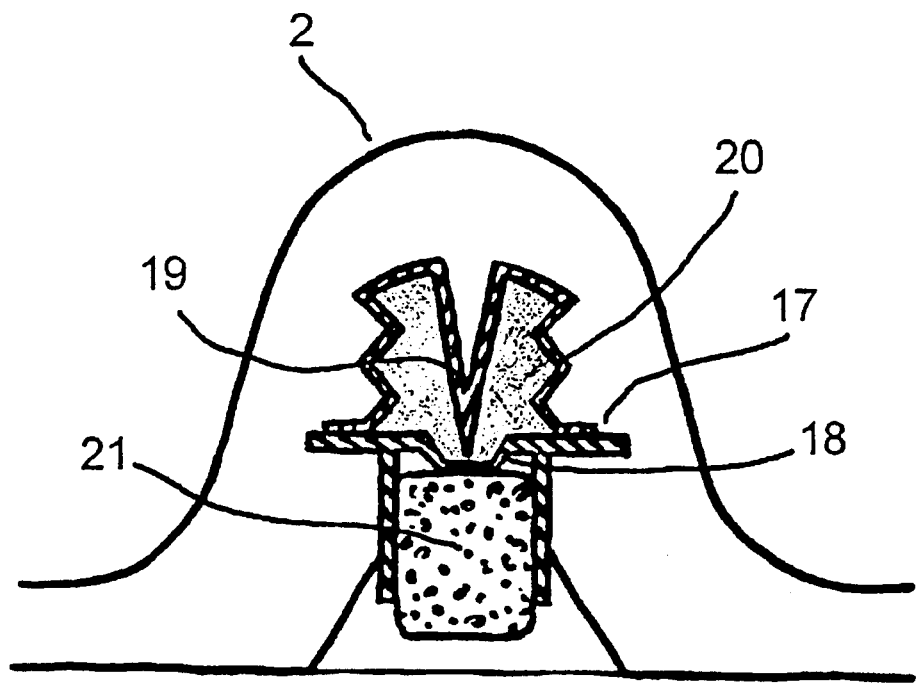
FIG. 7 shows the first element of the device in which the marking ink is contained in an individual container, which may be moulded in or separately exchangeable.

FIG. 7 shows the first element (2) of the device in which the marking ink is contained in an individual container (17) comprising ink, which container may be separately exchangeable. On the proximal side, the ink container is provided with a seal (18) which seal may be provided with cross- or star-shaped impressions serving as breaking initiators (not shown). The ink container (17) may be provided with an internal sharp point (19) for breaking the seal. In the embodiment shown the container (17) is provided with a felt-like printing pad (21) and is designed with deformable side walls (20) in such a way that when mounted in the siting device, the ink container is collapsible when applying a force on the top of the first element not greater than the force needed for bringing the central part of the cavity into contact with the skin.

Figure 8:
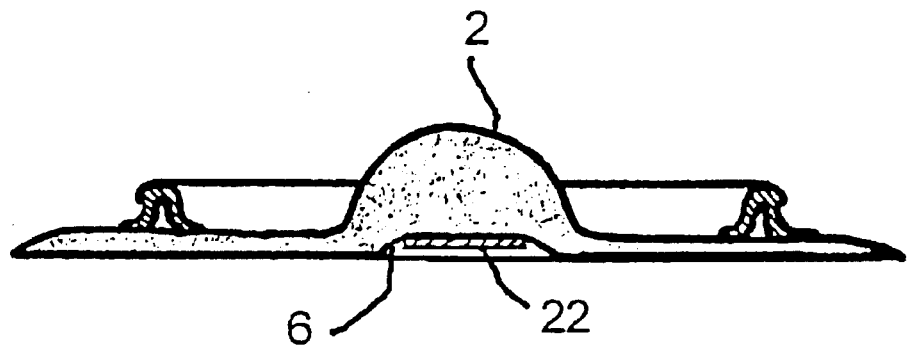
FIG. 8 shows the device in which the first element is provided with a cavity containing a transferable marking label.

FIG. 8 shows an embodiment of the device of the invention in which the first element (2) is provided with a cavity (6) containing a transferable marking label (22).

Figure 9:
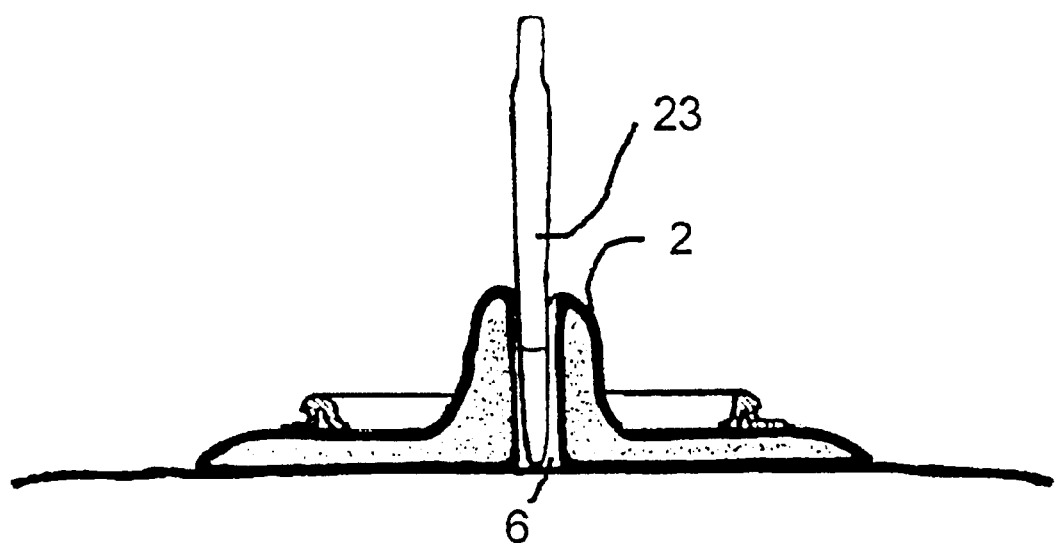
FIG. 9 shows an embodiment in which the first element is provided with a hole for guiding a marking pen.

FIG. 9 shows an embodiment in which the first element (2) is provided with a hole or cavity (6) in the form of a through-bore in the first element (2), said hole or cavity (6) having a diameter suitable for centering and guiding a marking pen (23).

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An ostomy siting device which can simulate a stoma in a chosen position and also represent an adhesive wafer and collection device for determining the chosen position of a possible stoma, comprising:
   a stoma simulating first element;
   a second element simulating an adhesive wafer of an ostomy appliance; and
   an adhesive surface on a proximal side of said ostomy siting device, said adhesive surface being suitable for repeated adhering to and removal from skin of an ostomate to be.

2. The ostomy siting device according to claim 1, wherein said second element has a centrally placed hole having a greater diameter than a part of said first element adapted to contact the skin, through which said first element can be placed in direct contact with the user's skin, so that said first and second elements are separately removable.

3. The ostomy siting device according to claim 2, wherein said adhesive surface is made from a permanently tacky silicone adhesive.

4. The ostomy siting device according to claim 3, wherein said device is provided with a centrally placed cavity.

5. The ostomy siting device according to claim 4, wherein said cavity is only in communication with the proximal side of said ostomy siting device.

6. The ostomy siting device according to claim 5, wherein said cavity contains a marking ink.

7. The ostomy siting device according to claim 6, wherein said marking ink is suitable for a permanent marking of the skin and is waterproof and resistant to disinfection of the skin.

8. The ostomy siting device according to claim 7, wherein said cavity contains a transferable marking label.

9. The ostomy siting device according to claim 6, wherein said ink is confined to a printing pad.

10. The ostomy siting device according to claim 9, wherein said printing pad is covered with a protecting cover strip having a lobe or ear extending outside said device, so that when marking is desired said protecting cover strip can be removed without moving said siting device from the chosen position.

11. The ostomy siting device according to claim 9, wherein the silicone material surrounding a proximal zone of said cavity has sufficient stiffness to allow a central part of said cavity and said printing pad to come into contact with the skin only when a force pressing on top of said first element is higher than 3 Newtons.

12. The ostomy siting device according to claim 6, wherein said cavity is provided with a valve.

13. The ostomy siting device according to claim 12, wherein the valve functions only when opposing sides of said first element are simultaneously pressed.

14. The ostomy siting device according to claim 6, wherein said cavity is provided with a separately mountable ink container.

15. The ostomy siting device according to claim 14, wherein said ink container is provided with a seal on a proximal side of said ink container which corresponds with the proximal side of said device when said ink container is mounted in said cavity.

16. The ostomy siting device according to claim 15, wherein said seal is provided with cross-shaped or star-shaped impressions serving as breaking initiators.

17. The ostomy siting device according to claim 15, wherein said ink container is provided with an internally mounted sharp point for breaking said seal.

18. The ostomy siting device according to claim 17, wherein, when mounted in said siting devices said ink container is collapsible by a force on a top of said first element not greater than a force needed for bringing a central part of said cavity into contact with the skin.

19. The ostomy siting device according to claim 15, wherein said ink container is provided with a printing pad on a proximal side of said seal.

20. The ostomy siting device according to claim 4, wherein said cavity is a through-bore in said device.

21. The ostomy siting device according to claim 20, wherein said cavity has a diameter suitable for centering and guiding a marking pen.

22. The ostomy siting device according to claim 1, wherein said first and second elements are made from permanently tacky silicone rubber material.

23. The ostomy siting device according to claim 22, wherein distal surfaces of said first and second elements are covered with a non-tacky polymer film.

24. An ostomy siting device for determining a desired position of a possible stoma, comprising:
- a stoma simulating first element for placement on skin of an ostomate to be in order to simulate a stoma in a chosen position; and
- a second element simulating an adhesive wafer of an ostomy appliance.

25. The ostomy siting device according to claim 24, wherein said second element has a centrally placed hole having a greater diameter than a part of said first element adapted to contact the skin, through which said first element can be placed in direct contact with the user's skin, so that said first and second elements are separately removable.

26. The ostomy siting device according to claim 24, further comprising an adhesive surface on a proximal side of said ostomy siting device, said adhesive surface being suitable for repeated adhering to and removal from the skin of the ostomate to be.

27. The ostomy siting device according to claim 24, wherein said first element is provided with a centrally placed cavity that contains a marking ink.

28. The ostomy siting device according to claim 27, wherein said cavity is provided with a separately mountable ink container that holds said marking ink.

* * * * *